US005772409A

United States Patent [19]
Johnson

[11] Patent Number: 5,772,409
[45] Date of Patent: Jun. 30, 1998

[54] DRUG INFUSION DEVICE WITH PRESSURE PLATE

[75] Inventor: Jay Gregory Johnson, Maple Plain, Minn.

[73] Assignee: SIMS Deltec, Inc., St. Paul, Minn.

[21] Appl. No.: 465,729

[22] Filed: Jun. 6, 1995

Related U.S. Application Data

[63] Continuation of Ser. No. 156,040, Nov. 22, 1993, abandoned.

[51] Int. Cl.[6] .................................................. F04B 43/08
[52] U.S. Cl. ........................ 417/360; 417/474; 604/153; 128/DIG. 12
[58] Field of Search ..................................... 604/151, 153, 604/264, 280, 284; 128/DIG. 12, DIG. 13; 417/474, 360, 477.1, 234, 477.2, 478; 248/65, 73, 506, 639

[56] References Cited

U.S. PATENT DOCUMENTS

| | | |
|---|---|---|
| D. 232,085 | 7/1974 | Benzing . |
| D. 247,820 | 5/1978 | Stuetzer . |
| D. 277,980 | 3/1985 | Bransky . |
| D. 294,733 | 3/1988 | Peterson et al. . |
| D. 326,153 | 5/1992 | Eastman et al. . |
| 3,402,673 | 9/1968 | Ballentine et al. . |
| 3,559,644 | 2/1971 | Stoft et al. . |
| 3,618,602 | 11/1971 | Shaw . |
| 3,620,650 | 11/1971 | Shaw . |
| 3,908,657 | 9/1975 | Kowarski . |

(List continued on next page.)

FOREIGN PATENT DOCUMENTS wo 93/10853  6/1993  WIPO .

OTHER PUBLICATIONS

Photographs of a pump product by Patient Solutions, Inc., Med–Mate ™, Model 1100, pp. A1–A5, Exhibit A.
Photographs of a pump product by Block Medical, Inc., a Hillenbrand Industry, Verifuse® Model No. B001500, pp. B1–B3, Exhibit B.
Photographs of a pump product by Medfusion, Inc., a Medex, Inc. Company, Infu–Med™, WalkMed™ 440 PIC, pp. C1–C2, Exhibit C.
Photographs of a pump product by C.R. Bard, Inc., Bard Medsystems Division, pp. D1–D3, Exhibit D.
Photographs of a pump product by Pharmacia Deltec, Inc., pp. E1–E2, Exhibit E.

(List continued on next page.)

*Primary Examiner*—Timothy Thorpe
*Assistant Examiner*—Peter G. Korytnyk
*Attorney, Agent, or Firm*—Merchant, Gould, Smith, Edell, Welter & Schmidt, P.A.

[57] ABSTRACT

An infusion system having a pumping mechanism with tube-engaging members for pumping fluid through a tube, a releasable pressure plate that can be attached and detached from the pumping mechanism having a releasable attachment mechanism for attaching an infusion tube to the pressure plate such that the infusion tube can be engaged by the tube-engaging members when the pressure plate is attached to the pumping mechanism, and an infusion tube for delivering fluid from a fluid source to a patient that is arranged and configured to be attached to the pressure plate by the attachment mechanism and used with the pumping mechanism. The infusion tube can be quickly replaced by detaching the infusion tube from the releasable attachment mechanism and attaching a new infusion tube to the pressure plate. The pressure plate preferably includes a pair of pump-securing extensions, a loop-shaped pump anchor, a plurality of tube-positioning rib pairs, and a retaining lip having a retaining lip surface sized to retain the infusion tube.

4 Claims, 6 Drawing Sheets

U.S. PATENT DOCUMENTS

| | | |
|---|---|---|
| 3,999,542 | 12/1976 | Shaw . |
| 4,010,749 | 3/1977 | Shaw . |
| 4,187,057 | 2/1980 | Xanthopoulos . |
| 4,224,882 | 9/1980 | Cruse . |
| 4,236,880 | 12/1980 | Archibald . |
| 4,256,437 | 3/1981 | Brown . |
| 4,274,407 | 6/1981 | Scarlett . |
| 4,282,867 | 8/1981 | Du Toit . |
| 4,322,201 | 3/1982 | Archibald . |
| 4,337,769 | 7/1982 | Olson . |
| 4,382,753 | 5/1983 | Archibald . |
| 4,398,908 | 8/1983 | Siposs . |
| 4,410,322 | 10/1983 | Archibald . |
| 4,451,255 | 5/1984 | Bujan et al. . |
| 4,468,221 | 8/1984 | Mayfield . |
| 4,482,347 | 11/1984 | Borsanyi . |
| 4,537,561 | 8/1985 | Xanthopoulos . |
| 4,559,038 | 12/1985 | Berg et al. . |
| 4,565,542 | 1/1986 | Berg . |
| 4,569,674 | 2/1986 | Phillips et al. . |
| 4,585,399 | 4/1986 | Baier . |
| 4,650,469 | 3/1987 | Berg et al. . |
| 4,657,486 | 4/1987 | Stempfle et al. . |
| 4,667,854 | 5/1987 | McDermott et al. . |
| 4,671,792 | 6/1987 | Borsanyi . |
| 4,673,334 | 6/1987 | Allington et al. . |
| 4,684,364 | 8/1987 | Sawyer et al. . |
| 4,735,558 | 4/1988 | Kienholz et al. . |
| 4,755,109 | 7/1988 | Botts . |
| 4,798,590 | 1/1989 | O'Leary et al. . |
| 4,845,487 | 7/1989 | Frantz et al. . |
| 4,861,242 | 8/1989 | Finsterwald . |
| 4,886,431 | 12/1989 | Soderquist et al. . |
| 4,978,335 | 12/1990 | Arthur, III . |
| 5,017,059 | 5/1991 | Davis . |
| 5,032,112 | 7/1991 | Fairchild et al. . |
| 5,074,756 | 12/1991 | Davis . |
| 5,078,683 | 1/1992 | Sancoff et al. . |
| 5,098,387 | 3/1992 | Wiest et al. . |
| 5,106,374 | 4/1992 | Apperson et al. . |
| 5,131,816 | 7/1992 | Brown et al. . |
| 5,147,313 | 9/1992 | Dikeman . |
| 5,165,874 | 11/1992 | Sancoff et al. . |
| 5,213,483 | 5/1993 | Flaherty et al. . |
| 5,219,327 | 6/1993 | Okada . |
| 5,226,886 | 7/1993 | Skakoon et al. . |
| 5,242,407 | 9/1993 | Struble et al. . |
| 5,249,937 | 10/1993 | Aubert . |
| 5,266,013 | 11/1993 | Aubert et al. . |
| 5,336,190 | 8/1994 | Moss et al. . |
| 5,397,222 | 3/1995 | Moss et al. . |
| 5,425,173 | 6/1995 | Moss et al. . |

OTHER PUBLICATIONS

Photographs of a pump product by AVI, Inc. AVI Guardian™ MICRO 110, pp. F1–F4, Exhibit F.

Photographs of a pump product by Abbott Laboratories, Abbott/Shaw LifeCare® Pump Model 3, pp. G1–G3, Exhibit G.

Patient Solutions, Inc. Directions for Use, MedMate™ 1100. 61 pages, Exhibit 2.

Block Medical, Inc. literature for VERIFUSE System, 1 page, dated Nov. 1990, Exhibit 3.

Medfusion, Inc. Operations Manual for Medfusion WALK-MED™ Ambulatory Infusion Pump, 92 pages, dated Apr., 1990, Exhibit 4.

Patient Solutions, Inc. literature for MedMate™ 1100, 2 pages, Exhibit 1.

Medex Ambulatory Infusion Systems literature, entitled "WalkMed Pump Disposable Products," 2 pages, dated 1992, Exhibit 5.

Medex Ambulatory Infusion Systems literature, entitled "WalkMed PCA," 2 pages, dated 1993, Exhibit 6.

Bard Ambulatory PCA Pump literature, 2 pages, dated Jun. 1990, Exhibit 7.

Bard MedSystems Division, C.R. Bard, Inc., Quick Reference Guide, 2 pages, dated Feb. 1992, Exhibit 8.

Bard MedSystems Division, C.R. Bard, Inc., Bard® Ambulatory PCA Pump Operator's Manual, 43 pages, dated Apr. 1990, Exhibit 9.

AVI, Inc. literature entitled "The AVI Adantage,", 2 pages, dated 1983, Exhibit 10.

AVI, Inc. literature, entitled "Bridging the Gap," 6 pages, dated Apr. 22, 1983, Exhibit 11.

Abbott Laboratories Hospital Products Division literature, entitled "The Blue Line System LifeCare®," 12 pages, dated Jul., 1990, Exhibit 12.

Abbott Laboratories Hospital Products Division literature, entitled "LifeCare® Electronic Flow Control Systems Catalog," 34 pages, dated May, 1985, Exhibit 13.

DRUG INFUSION DEVICE WITH PRESSURE PLATE

This is a continuation of application Ser. No. 08/156,040, filed Nov. 22, 1993, now abandoned, which application is incorporated herein by reference.

FIELD OF THE INVENTION

The invention relates to infusion pumps and more particularly to infusion tubes and pressure plates for use with an infusion pump.

BACKGROUND OF THE INVENTION

Currently, drugs or other fluids are often administered to patients intravenously through the use of a drug infusion pump. One commonly-used type of drug infusion pump is a linear peristaltic drug infusion pump as shown in FIG. 1. This type of pump typically includes a peristaltic pump mechanism 12 having tube-engaging members 13 and a pump pressure plate 11. The main surface of the pump pressure plate 11 contains a plurality of oppositely disposed ribs with a channel between each pair of oppositely-disposed ribs. A compressible tube 46 is attached to the pressure plate by threading the tube through an aperture 45 in one end of the pressure plate through a pump anchor 28 and through ring 47 at an opposite end. The compressible tube is then secured to the pump pressure plate and positioned in the channels by use of ring 47 and restraint 44 which is force-fitted into the aperture 45. Together, tube 46 and pressure plate 11 form a tube/pressure plate assembly 50.

Tube/pressure plate assembly 50 is then attached to peristaltic pump mechanism 12 by pump-securing extensions 24 on pressure plate 11 which engage a suspended pin assembly 14 having support structures 15 and pins 16 which are located on the bottom of the pump mechanism. The pump anchor 28 located on the pressure plate 11 engages a releasable securing mechanism inside the pump mechanism 12 to secure the pressure plate to the pump mechanism 12. During use, the tube-engaging members act in a predetermined sequence to draw a predetermined amount of fluid into the compressible tube and then expel the predetermined amount of fluid from the tube to the patient.

Because of medical safety reasons, any portions of the device which might come in fluid contact with the patient during use must be disposed of after use. Therefore, the compressible tube must be changed after use. Unfortunately, because of the complex nature in which the compressible tube is connected to the pump pressure plate, including the need to thread the tube through the aperture, the anchor, and the securing ring, it is impractical to change the tube after each use. Therefore, when it is necessary to provide a new tube, both the tube and pressure plate are disposed of as a single unit and are replaced with a new tube/pressure plate assembly for use with the next patient. This practice causes an unwanted increase in the amount of medical waste and cost of using this type of pump.

Therefore, there arises a need for an infusion device which has an infusion tube which is easily attached to and removed from a pump pressure plate.

SUMMARY OF THE INVENTION

The present invention is for an infusion tube and releasable pressure plate for use with a pumping mechanism having tube-engaging members. The releasable pressure plate is preferably arranged and configured so that it can be attached and detached from the pumping mechanism. The infusion tube is attached to the pressure plate by a releasable attachment mechanism which attaches the infusion tube to the pressure plate such that the infusion tube can be engaged by the tube-engaging members and so that the infusion tube can be detached from the pressure plate and replaced with a second infusion tube.

The present invention meets the need for an infusion device having a disposable infusion tube by the use of an infusion tube and a releasable attachment mechanism which secures the infusion tube to the pressure plate. Unlike the current designs, the present invention enables the infusion tube to be securely and yet releasably attached to the pressure plate without the need for threading the tube through various openings in the pressure plate. Therefore, the present invention enables a doctor or nurse to attach a new sterile infusion tube to a pressure plate very quickly. The ability to quickly dispose of old infusion tubes and replace them with new tubes enables the pressure plate to be removed, and sterilized if desired, thereby eliminating the need to dispose of the pressure plate, reducing medical waste and reducing the cost for using these types of infusion pumps. The pressure plate can remain with the patient for multiple therapies with different infusion tubes, each tube being discarded after use.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

In the drawings, wherein like reference letters and numerals indicate corresponding elements throughout the several views.

DETAILED DESCRIPTION OF THE PREFERRED EMBODIMENT(S)

Figure 1:
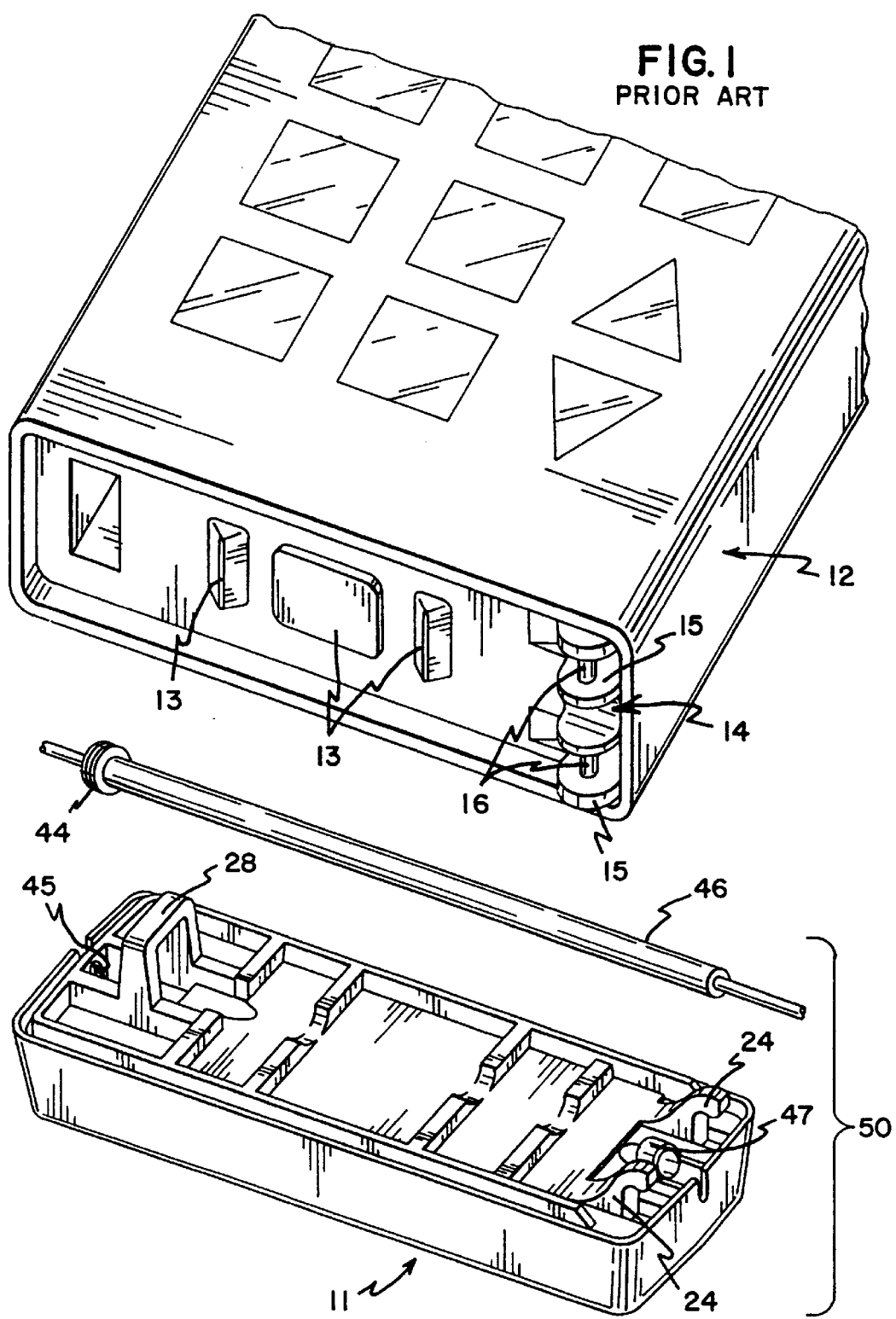
FIG. 1 is a perspective view of a prior art version of an infusion pump with portions broken away.
Figure 2:
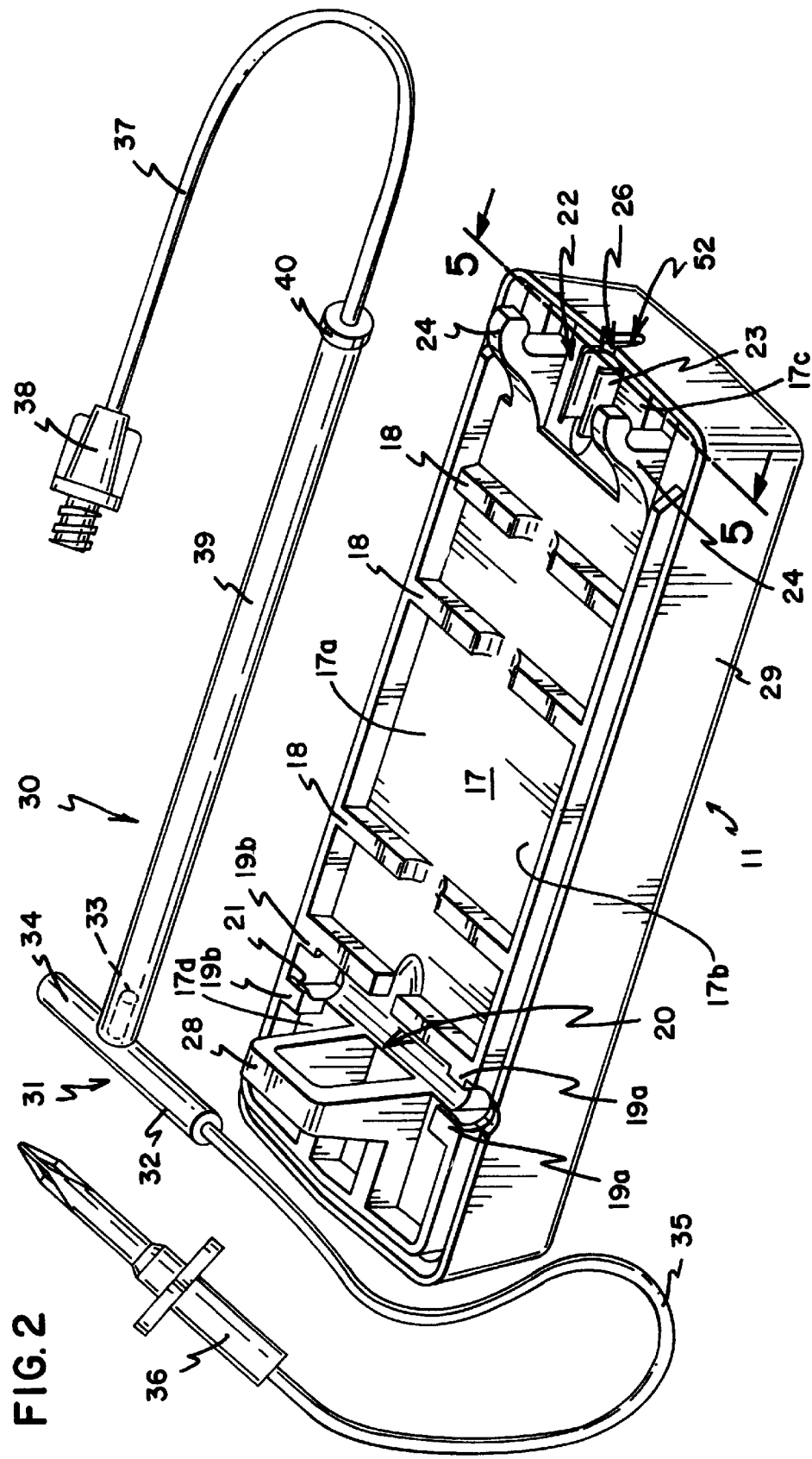
FIG. 2 is a perspective view of a first embodiment of a pressure plate and a disposable infusion tube in accordance with the invention.

Referring now to the drawings, wherein like reference numerals designate like parts, one preferred embodiment of the invention is a disposable drug infusion tube 30 and a pump pressure plate 11, as shown in FIG. 2, for use with a linear peristaltic drug infusion pump (not shown). During use, the disposable drug infusion tube 30 is attached to the pressure plate 11 and then the pressure plate 11 is attached to a peristaltic pump mechanism 12 as shown in FIG. 1 and described in the Background of the Invention section herein.

Referring now to FIG. 2, the pump pressure plate 11 has a plurality of rib pairs 18 located on a substantially flat main surface 17. Pump pressure 11 has first and second lungitudinal sides 17*a*, 17*b*, and first and second transverse ends 17*c*, 17*d*. The ribs of each rib pair 18 are each oppositely disposed from one another forming a channel for positioning a portion of the disposable drug infusion tube 30 beneath the tube-engaging members 13 of the peristaltic pump mechanism 12.

The disposable drug infusion tube 30 would be comprised of a T-shaped connector 31, a first tube 35, a second tube 37 and a third tube 39 between the T-shaped connector 31 and the second tube 37. The first tube 35 would also preferably be connected to a means for providing a fluid source to the first tube 35, such as an intravenous bag spike 36. Bag spike 36 interconnects first tube 35 with an i.v. bag of fluid (not shown). Similarly, the distal end of the second tube 37 would be connected to a means for providing a fluid source to a patient, such as a threaded connector 38, for example, a Luer lock connector, that is capable of being attached to a patient's i.v. line. Other conduit connector structures are possible for either or both of bag spike 36 or threaded connector 38.

Figure 7:
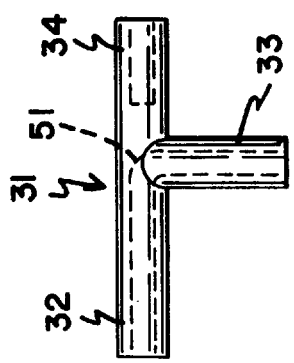
FIG. 7 is a top plan view of the preferred embodiment of a connector for use with the invention.

The T-shaped connector 31, best shown in FIG. 7, would preferably have a first arm 32, a second arm 33 and a third arm 34 that are arranged such that the first arm 32 and third arm 34 are parallel and attached to the second arm 33. The second arm 33 would be attached such that it would be perpendicular to the first arm 32 and third arm 34 and aligned with the channel between the nearest pair of oppositely disposed ribs 18. Preferably, third arm 34 has a longitudinal axis concentric with a longitudinal axis of the first arm 32.

The first arm 32 would be connected to the first tube 35 and would have an internal fluid passage such that a continuous fluid passage is present from the first tube 35 through the first arm 32. The second arm 33 would also have an internal fluid passage and would be connected to the first arm 32 and third tube 39, such that a continuous fluid passage existed between the first tube 35, first arm 32, second arm 33 and third tube 39. The third arm 34 could be solid or partially recessed and sealed toward a central portion 51 of connector 31 to prevent the leaking of any fluid through the third arm 34 as shown in FIG. 7. Those skilled in the art would recognize that the present invention could be practiced without the third arm 34. However, the use of a third arm 34 is preferred for use with the releasable clamping means as described later. Also, third arm 34 could be disposed at an angle different than 90° relative to second arm 33.

Referring now to FIG. 2, the third tube 39 would be attached to the second arm 33 by sliding an end of the third tube 39 over the second arm 33. Similarly, the third tube 39 would be attached to the second tube 37 by sliding an end of the third tube 39 over an end of the second tube 37. The third tube 39 would also be made from a resilient material such that the third tube 39 could be compressed against the main surface 17 by the tube-engaging members 13 to shut off the flow of fluid in the third tube 39 or to expel a predetermined amount of fluid from the third tube 39 to the second tube 37. Those skilled in the art would recognize that the use of a third tube 39 is not required for practicing the present invention. Instead, the second tube 37 could be compressible and resilient and attached directly to the second arm 33. However, the use of a separate third tube 39 attached to the second tube 37 is preferred because it provides the ability to utilize second tubes 37 having different tube compression properties or to use different third tubes 39 with different diameters and flow capacities.

Releasable attachment means would also be provided to hold the drug infusion tube 30 to the pressure plate 11. In one preferred embodiment, releasable clamping means would be used to hold the connector 31 to the pressure plate 11 at one end of plate 11 and a releasable securing means would be used to hold the second tube 37 and third tube 39 to the pressure plate 11 at an opposite end of plate 11. Those skilled in the art would recognize that different combinations and numbers of clamping means and securing means could be used as the attachment means in the present invention. The releasable attachment means can also include other attachment structures for temporarily mounting drug infusion tube 30 to pressure plate 11, such as an interference fit or other mechanical structures which can be selectively operated to mount tube 30 to plate 11.

Figure 4:
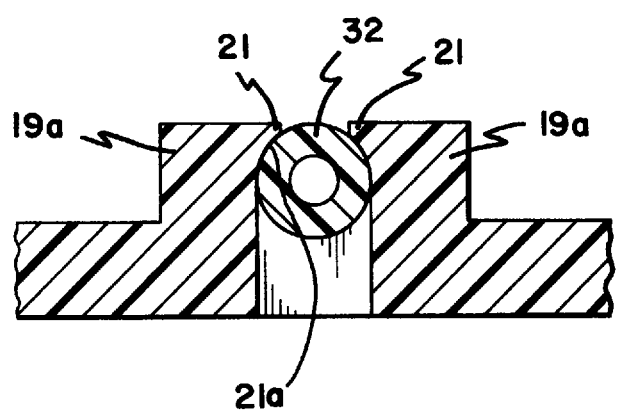
FIG. 4 is a localized cross-sectional view of FIG. 3 as shown along section 4—4.

In one preferred embodiment, the releasable clamping means would be arranged and configured such that the connector 31 could be easily attached and detached from the pressure plate 11. As shown in FIGS. 2 and 4, the preferred clamping means would be a recess 20 in the main surface 17 of the pressure plate 11 extending across the width of the pressure plate 11, and two pairs of clamping ribs 19*a,b*, one pair being located at each end of the recess 20 with one clamping rib 19*a,b* being oppositely disposed across the recess 20 from another clamping rib 19*a,b*. The clamping ribs 19*a,b* would preferably have a lip 21 with a retaining lip surface 21*a* extending over the recess 20 to secure the connector 31.

Figure 3:
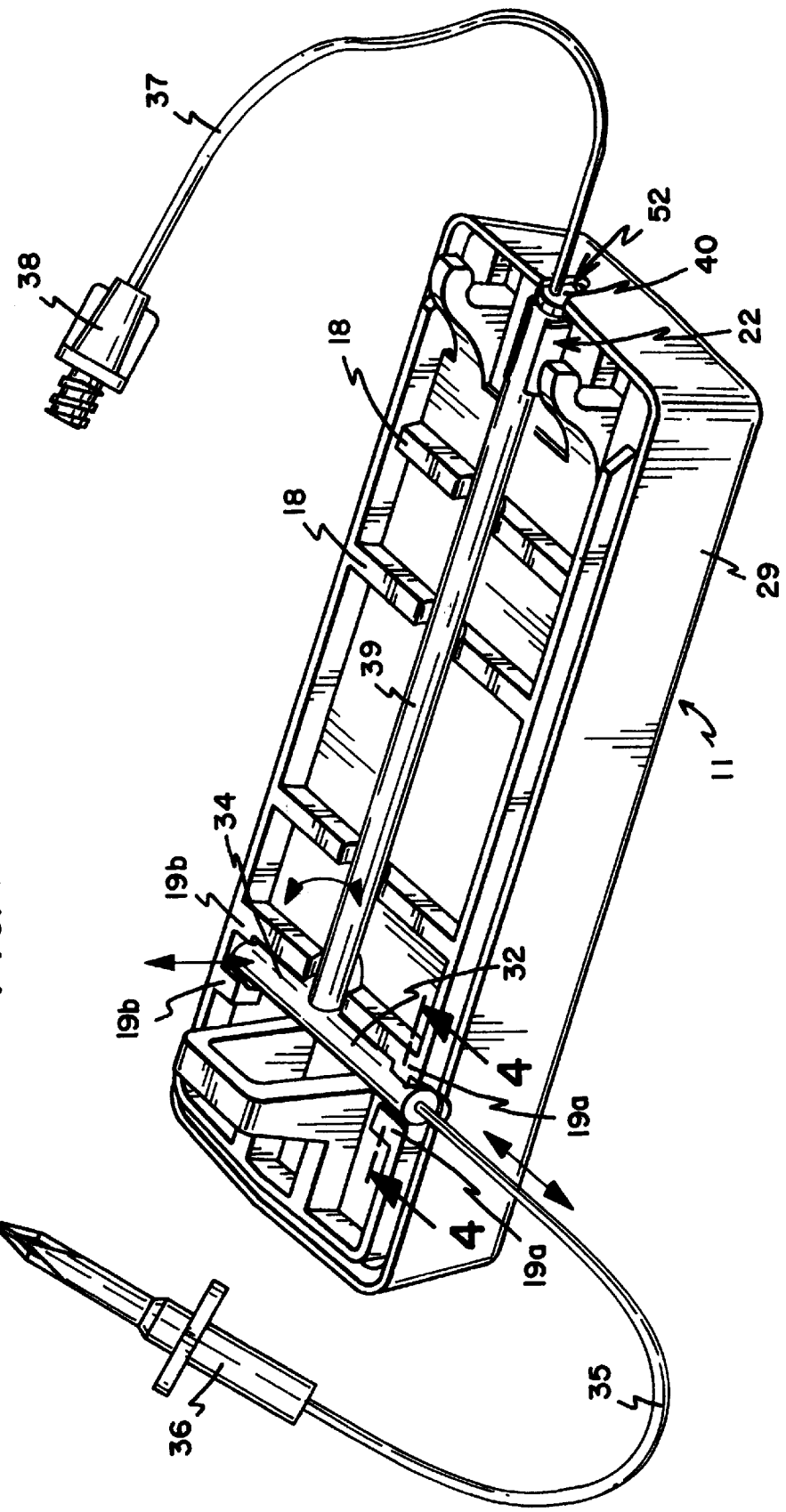
FIG. 3 is a perspective view of FIG. 2 showing the disposable infusion tube connected to the pressure plate.

A first method for clamping the connector 31 to the main surface 17 would be to position the second arm 33 away from the main surface 17 of the pump pressure plate 11. The third arm 34 of the connector 31 is then slidably inserted into the recess 20 between the first set of clamping ribs 19*a* until the third arm 34 is between the second set of clamping ribs 19*b* and the first arm 32 is between the first pair of clamping ribs 19*a*. The connector 31 is then rotated about the longitudinal axis defined by first arm 32 until the third tube 39 is located in the channel between the ribs 18 as shown in FIG. 3. To remove the connector 31 from the clamping means, the connector 31 would be rotated until the second arm 33 clears clamping ribs 19*a*, the first arm 32 and third arms 34 are then slid out of the recess 20.

A second method for clamping the connector 31 to the main surface 17 would be to position the third arm 34 above the second pair of clamping ribs 19*b* and the first arm 32 above the first pair of clamping ribs 19*a* while aligning the second arm 33 with the channel between the ribs 18. Because the connector 31 and clamping ribs 19*a,b* are somewhat resilient, the first arm 32 and third arm 34 of the connector 31 could be pushed downward, as shown in FIG. 3, between the clamping rib lips 21 until the connector 31 is snapped into the recess 20. The connector 31 could then be unclamped from the pressure plate 11 by pulling upward on the connector 31 or tube 39 until the connector 31 was unsnapped from the recess 20 and clamping ribs 19*a,b*. It is to be appreciated that other methods in accordance with the invention include sliding or snapping connector 31 into recess 20 and then the other of sliding or snapping connector 31 from recess 20. Those skilled in the art would also recognize that other releasable clamping means, such as tabs, notches, snaps, or the like, could be used with the present invention.

To ensure that the first arm 32 and third arm 34 are not inadvertently inserted in the wrong position, the preferred embodiment would utilize a first arm 32 having a different length than the third arm 34. Because the lengths are different, there is only one way for the user to position the connector 31 over the pressure plate 11 such that the second arm 33 and third tube 39 are positioned in the channels between the oppositely-disposed ribs 18. Therefore, the preferred embodiment also provides the added assurance that the drug infusion tube 30 is always properly aligned in the pressure plate.

Figure 5:
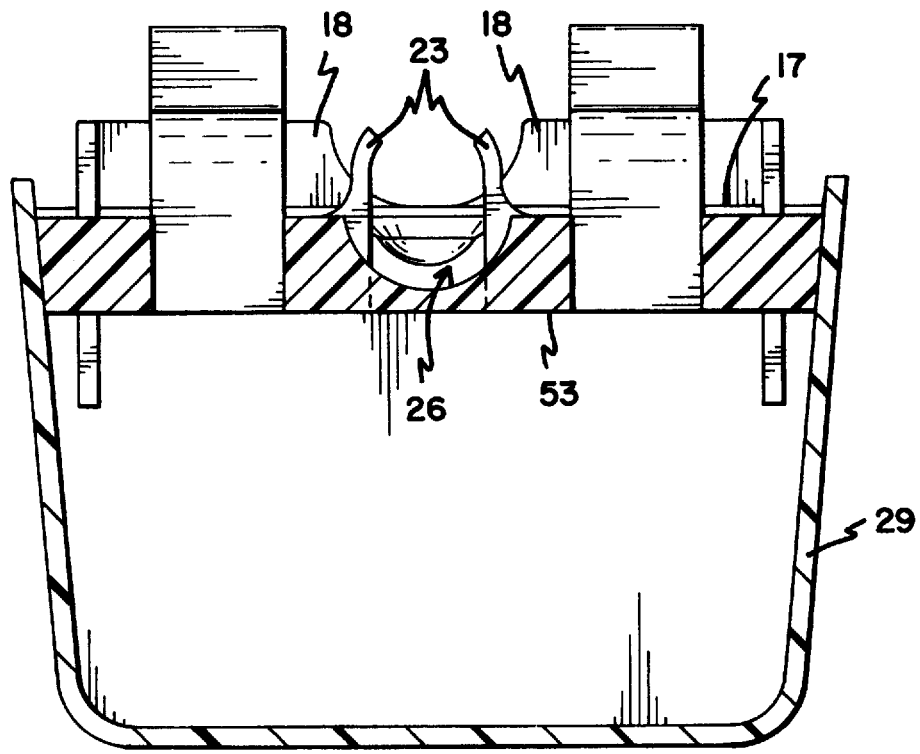
FIG. 5 is a localized cross-sectional view of FIG. 2 as shown along section 5—5.

As discussed earlier, in addition to the releasable clamping means for clamping the T-shaped connector 31, one preferred embodiment of the invention also includes a releasable securing means for securing the second tube 37 and the third tube 39 to the pressure plate 11. As shown in FIGS. 2 and 5, one means for securing the second tube 37 and third tube 39 to the pressure plate 11 is to attach a locating ring 40 to the third tube 39 such that the locating ring 40 is adjacent to the second tube 37. An expandable securing clip 22 is also attached to the main surface 17 of the pressure plate 11 adjacent to a securing ring recess 26 located in the pressure plate 11.

In one preferred embodiment, the expandable securing clip 22 would have curved lips or extensions 23 protruding from the main surface 17 that are spaced apart to allow the insertion of the third tube 39 in another preferred embodiment. The securing ring recess 26 would be positioned between the securing clip 22 and the end surface of the pump pressure plate 11 and would have a width such that the locating ring 40 would fit snugly into the securing ring recess 26 between the securing clip 22 and the end surface of the pump pressure plate 11, best shown in FIG. 3. The securing clip 22 and securing ring recess 26 would also preferably be located on an axis extending through the channel formed between the nearest pair of oppositely disposed ribs 18 such that the third tube 39 would be properly aligned with the channel. Second tube 37 fits into a slot 52 formed in an end of pressure plate 11. Locating ring 40 will not fit into the securing clip 22 or the slot 52, to ensure that third tube 39 is not improperly stretched or compressed in a direction along a longitudinal axis of tube 39.

Because the third tube 39 is compressible, the third tube 39 can be easily inserted and removed from the securing clip 22. Moreover, because the locating ring 40 is provided, the third tube 39 is always properly located on the pressure plate 11. Therefore, this securing means provides an easy and reliable way for the second tube 37 and third tube 39 to be secured to or removed from the pressure plate 11 and to ensure that the third tube 39 is properly aligned on the pressure plate 11.

Figure 6:
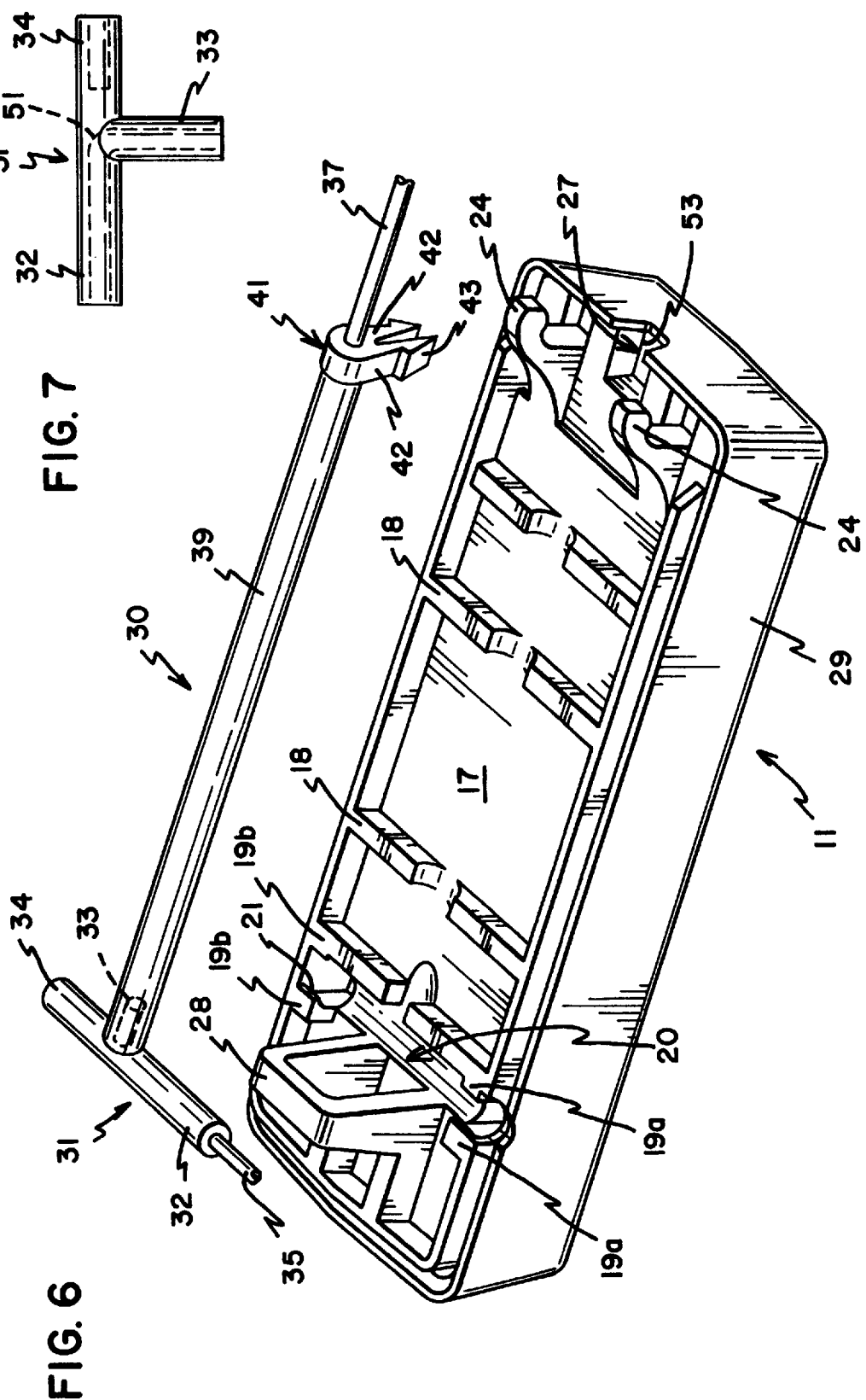
FIG. 6 is a perspective view of a second embodiment of a pressure plate and a disposable infusion tube in accordance with the invention.

As shown in FIG. 6, a second means for securing the second tube 37 and third tube 39 to the pressure plate 11 would be to use an expandable snap 41 attached to the second tube 37 such that the snap 41 is adjacent to the third tube 39 in another preferred embodiment. The expandable snap 41 would be arranged and configured to fit into a snap aperture 27 in the pump pressure plate 11. The expandable snap 41 would have two parallel extensions 42 with triangular portions 43 extending outward from the parallel extensions 42. The second tube 37 and third tube 39 would be secured to the pressure plate 11 by inserting the snap 41 into the snap aperture 27. The triangular portions 43 then act to catch on the lip or edge of bottom surface 53 of the main surface 17 of the pressure plate 11 to prevent the removal of the snap 41, second tube 37 and third tube 39 from the pressure plate 11.

To remove the second tube 37 and third tube 39, the parallel extensions 42 of the snap 41 are pressed inward until the triangular portions 43 are within the snap aperture 27. The snap 41 is then lifted from the snap aperture 27. However, because the snap 41 is made from an expandable material, the snap 41 could also be removed by simply pulling upward on the snap 41 until the extensions 42 moved inward and out of the snap aperture 27. Similarly to the previously-described securing means embodiment, the snap aperture 27 would be aligned in an axis extending through the channel between the nearest pair of oppositely-disposed ribs 18 to ensure that the third tube 39 is properly positioned between the oppositely-disposed ribs 18. Those skilled in the art would recognize that other releasable securing means could be used with the present invention.

A second clamping means including a connector, like connector 31, could be used to hold the second and third tubes 37,39 to the pressure plate 11. In that case, the second connector would be between second tube 37 and third tube 39 in a mirror image configuration to connector 31, and appropriate clamping means would be provided to releasably hold the second connector to the pressure plate 11.

Figure 8:
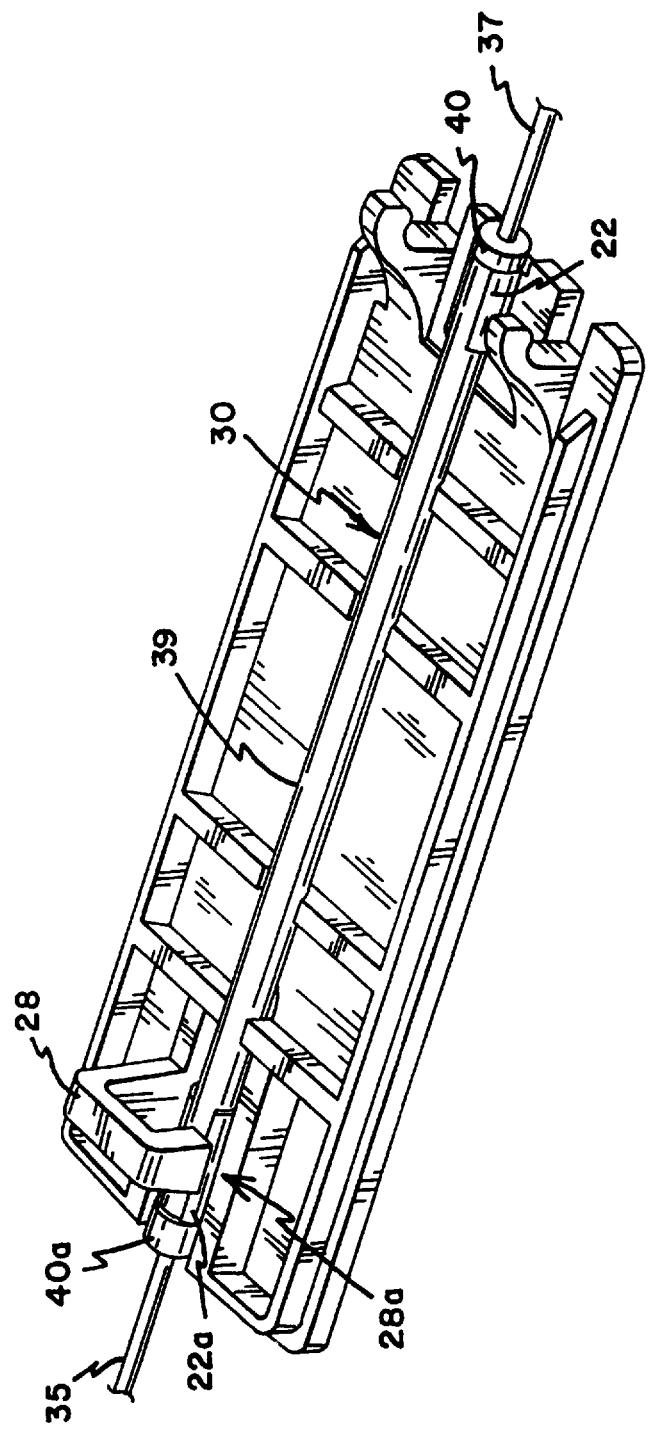
FIG. 8 is a perspective view of a third embodiment of a pressure plate and a disposable infusion tube.

It is to be appreciated that two releasable securing means, such as securing clips 22,22a, may be provided, one on each end of third tube 39 as shown schematically in another preferred embodiment in FIG. 8. First tube 35 would connect to third tube 39 in a similar manner as second tube 37 does in the embodiment of FIGS. 2 and 3. Drug infusion tube 30 would be threaded through pump anchor 28 in the configuration of anchor 28 in FIGS. 2 and 3. Alternatively, a slot 28a may be provided in pump anchor 28 to permit drug infusion tube 30 to be inserted into an interior of pump anchor 28 in a direction perpendicular to the longitudinal direction of third tube 39, without having to thread any members of drug infusion tube 30 through the aperture defined by pump anchor 28. A second locating ring 40a could be provided with a different dimension than the first ring 40 so that a mechanical fit/non-fit arrangement is provided to assure proper placement of drug infusion tube 30. Two expandable snaps 41 of the type shown in FIG. 6 could be provided in a similar manner on opposite ends of third tube 39, instead of rings 40,40a and securing clips 22,22a. Alternatively, the second releasable securing means could include ring 40/clip 22 or snap 41 if the other of snap 41 or ring 40/clip 22 is provided for the first releasable securing means.

The pressure plate 11 could be preferably made from an injection molded rigid polymer. For example, long fiberglass-filled polyurethane would likely be acceptable. The lower portion 29 of the pressure plate 11 would be injection molded as one part and the main surface 17, ribs 18, clamping means, securing means, pump anchor 28 and pump securing extensions 24 would be injection molded as a second part. Because the pressure plate 11 is molded as two parts, the clamping ribs 19a,b can be easily molded from either the side or bottom of the mold. The main surface 17 would then be fastened to the lower portion 29 by use of an adhesive, snap arrangement or any other suitable fastening means. Those skilled in the art would recognize that the pressure plate 11 could be made from other materials or made by other methods as long as the main surface 17 of the pressure plate 11 were rigid enough to allow the tube engaging members 13 to compress the third tube 39 between the tube engaging members 13 and the pressure plate 11. Tube 35 and tube 39 are preferably adhesively attached with a solvent bond to connector 31, and tube 37 is preferably adhesively attached with a solvent bond to tube 39. Tubes 35, 37, 39 are preferably made from polyvinylchloride (PVC). Connector 31 is made from plastic, such as polycarbonate or PVC. Ring 40 and snap 41 are also made of plastic, such as polycarbonate or PVC.

Once infusion tube 30 is attached or otherwise mounted to pressure plate 11, and pressure plate 11 is attached or otherwise mounted to pump mechanism 12, fluid, including fluids containing a drug or drugs, is pumped from the fluid source to a distal end of second tube 37, which my be connected to a patent.

The releasable attachment structure for mounting infusion tube 30 to pressure plate 11, including, for example, connector 31 and associated clamping structure, securing clip 22 and ring 40, or expandable snap 41, and other releasable attachment structure permits infusion tube 30 to be securely and temporarily mounted to pressure plate 11. Such releasable attachment permits reuse of plate 11, saving costs for the caregiver and patient.

The releasable attachment of plate 11 from both tube 30 and pump mechanism 12 permits plate 11 to be sterilized between uses with different infusion tubes 30. Such would be difficult, or impossible if plate 11 was permanently affixed to pump mechanism 12, and infusion tube 30 was permanently attached to plate 11.

It is to be appreciated that advantages of the present invention can be realized through the use of the releasable attachment structure for mounting infusion tube 30 to plate 11, regardless of the attachment structure between plate 11 and pump mechanism 12, whether it is permanent (for example, a hinge) or releasable (for example, anchor 28 and extensions 24).

Although characteristics and advantages, together with details for structure, materials, function and process steps, have been described in reference to a preferred embodiment herein, it is understood that the disclosure is illustrative. To that degree, various changes made, especially to matters of shape, size and arrangement, to the full extent extended by the general meaning of the terms in which the appended claims are expressed, are within the principles of the present invention.

What is claimed is:

1. A pressure plate for use with a control module of a pump comprising:

a body having a main surface facing in a first direction and including first and second longitudinal sides, and first and second transverse ends;

a pair of hook-shaped pump-securing extensions extending from the main surface adjacent to the first transverse end;

a loop-shaped pump anchor extending from the main surface adjacent to the second transverse end;

a plurality of tube-positioning rib pairs extending from the main surface and spaced apart to receive an infusion tube in a direction generally parallel to the first and second longitudinal sides; and a retaining lip extending from the main surface and having a retaining lip surface spaced from the main surface and sized to retain the infusion tube releasably held by the retaining lip surface to the main surface, the hook-shaped pump-securing extensions and the loop-shaped pump anchor engageable with the control module to mount the body to the control module.

2. The pressure plate of claim 1, wherein the loop-shaped pump anchor includes an end defining a gap between the end of the loop-shaped pump anchor and the main surface of the body, the gap sized to receive a portion of the infusion tube.

3. The pressure plate of claim 1, further comprising an infusion tube mounted to the pressure plate.

4. The pressure plate of claim 3, further comprising a kit including a plurality of infusion tubes, each infusion tube being successively mounted to the pressure plate by the retaining lip.

* * * * *

UNITED STATES PATENT AND TRADEMARK OFFICE
CERTIFICATE OF CORRECTION

PATENT NO. : 5,772,409

DATED : June 30, 1998

INVENTOR(S) : Johnson

It is certified that error appears in the above-identified patent and that said Letters Patent is hereby corrected as shown below:

In column 3, line 8, insert —plate— after the word "pressure".

Signed and Sealed this

Nineteenth Day of October, 1999

Attest:

Q. TODD DICKINSON

*Attesting Officer*   *Acting Commissioner of Patents and Trademarks*